US00PP30012P2

(12) United States Plant Patent
Zaiger et al.

(10) Patent No.: US PP30,012 P2
(45) Date of Patent: Dec. 25, 2018

(54) PEACH TREE NAMED 'APRIL ZEE'

(50) Latin Name: *Prunus persica*
Varietal Denomination: April Zee

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 15/731,741

(22) Filed: Jul. 27, 2017

(51) Int. Cl.
*A01H 5/08* (2018.01)

(52) U.S. Cl.
USPC ..... Plt./197
CPC ..... *A01H 5/08* (2013.01)

(58) Field of Classification Search
USPC ..... Plt./197
See application file for complete search history.

(56) References Cited

U.S. PATENT DOCUMENTS

PP27,168 P2 * 9/2016 Zaiger ..... A01H 6/7463 Plt./197

* cited by examiner

*Primary Examiner* — Anne Marie Grunberg

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size fruit.
3. Clingstone fruit with firm, yellow flesh.
4. Fruit with good flavor and eating quality.
5. Fruit having an attractive red skin color.

1 Drawing Sheet

Botanical designation: *Prunus persica.*
Variety denomination: 'April Zee'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, 'Super Lady' Peach (U.S. Plant Pat. No. 15,578), 'Super Zee' Peach (U.S. Plant Pat. No. 17,874) and our non-patented proprietary peach seedling selections '390LU304', '211LK116', '7LL75', '53ZH1029' and '37ZD706'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from a first generation cross between our proprietary non-patented peach seedlings '390LU304' and '53ZH1029'. The seed parent (390LU304) originated as a first generation cross between the non-patented proprietary peach seedling selections with the field identification numbers '211LK116' and '7LL75'. The pollen parent (53ZH1029) originated as a first generation cross between the non-patented proprietary peach seedling selection with the field identification number '37ZD706' and 'Super Lady' Peach (U.S. Plant Pat. No. 15,578). A large number of these first generation crosses were budded to older trees of 'Nemaguard' Rootstock (non-patented) to accelerate rapid fruit production. Under close and careful observation we recognized the desirable tree and fruit characteristics of the present seedling and selected it in 2010 for additional asexual propagation and commercialization.

ASEXUAL REPRODUCTION OF THE VARIETY

In 2010 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of peach tree (*Prunus persica*) is of large size, vigorous, upright growth and a regular and productive bearer of large size, yellow flesh, clingstone fruit with good flavor and eating quality. The fruit is further characterized by having firm flesh and attractive red skin color. In comparison to its proprietary non-patented peach seed parent '390LU304' the fruit of the new variety has a lower chilling requirement of 200 hours compared to 400 hours and is approximately 1 week earlier in maturity. In comparison to its proprietary non-patented peach pollen parent '53ZH1029' the fruit of the new variety has better eating quality and is approximately 5 days later in maturity. In comparison to the commercial variety 'Super Zee' Peach (U.S. Plant Pat. No. 17,874) the fruit of the new variety is larger in size.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 7 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height the first growing season. Varies slightly with type and fertility of soil, climatic conditions and cultural practices.

*Form*.—Upright, usually pruned to vase shape.

*Branching habit*.—Upright, crotch angle approximately 25°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 6 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 200 hours at or below 45° F.

Trunk:

*Size*.—Large, average circumference 66.0 cm at 22.9 cm above ground on a 7 year old tree.

*Stocky*.—Medium stocky.

*Texture*.—Medium shaggy, roughness increases with age.

*Color*.—Varies from 2.5Y 3/2 to 2.5Y 2/2.

Branches:

*Size*.—Medium. Average circumference 23.1 cm at 1.2 meters above ground. Crotch angle approximately 25°, increases with heavy crop load.

*Surface texture*.—New growth relatively smooth. Mature growth medium rough, roughness increases with age.

*Lenticels*.—Average number 12 in a 25.8 square cm area. Average length 5.0 mm. Average width 2.4 mm. Color varies from 10YR 6/6 to 10YR 5/6.

*Color*.—New growth varies from 2.5GY 6/4 to 2.5GY 6/6. Mature growth varies from 7.5YR 3/2 to 7.5YR 3/4, varies with age of growth.

Leaves:

*Size*.—Large. Average length 144.9 mm. Average width 49.2 mm.

*Form*.—Lanceolate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 8.1 mm. Average width 1.7 mm. Longitudinally grooved. Surface — glabrous. Color 2.5GY 6/6.

*Glands*.—Type — eglandular, none present.

*Stipules*.—Average number 2. Average length 7.8 mm. Edges pectinate. Color varies from 5GY 5/4 to 5GY 5/6.

*Color*.—Upper surface varies from 7.5GY 3/6 to 7.5GY 4/6. Lower surface varies from 5GY 5/6 to 5GY 4/6. Midvein color 2.5GY 6/6.

Flower buds:

*Size*.—Large. Average length 21.9 mm. Average diameter 13.0 mm.

*Hardiness*.—Hardy with respect to California winters.

*Density*.—Dense.

*Form*.—Conical, becoming elongated just before opening.

*Pedicel*.—Large. Average length 6.5 mm. Average width 1.5 mm. Surface — glabrous. Color varies from 5GY 6/8 to 10R 3/8.

*Color*.—Varies from 2.5RP 8/6 to 5RP 8/6.

Flowers:

*Blooming period*.—Date of First Bloom Feb. 5, 2017. Date of Petal Fall Feb. 15, 2017, varies slightly with climatic conditions.

*Size*.—Large, showy. Average height 22.2 mm. Average diameter 47.3 mm.

*Petals*.—Normally 5, alternately arranged to sepals. Size — large. Average length 25.5 mm. Average width 22.6 mm. Form — ovate. Petal apex — rounded. Petal base — truncate. Margin — entire. Arrangement — free to slightly overlapping. Both upper and lower surfaces glabrous. Color varies from 5RP 8/4 to 7.5RP 8/4, fades with age of flower.

*Sepals*.—Normally 5, alternately arranged to petals. Size — large. Average length 7.2 mm. Average width 6.5 mm. Shape — ovate. Apex — rounded to triangular. Margin — entire. Color — upper surface varies from 5GY 5/8 to 2.5GY 5/8. Lower surface varies from 5R 2/6 to 2.5GY 5/6. Surface — upper surface glabrous, lower surface pubescent.

*Stamens*.—Average number per flower 42. Average filament length 16.6 mm. On average, the stamens are above the height of the petals. Filament color varies from N 9.5/(white) to 2.5RP 7/8. Anther color varies from 10R 3/10 to 7.5Y 8/8.

*Pollen*.—Self fertile. Color varies from 5Y 7/2 to 5Y 6/10.

*Pistil*.—Number — normally one. Average length 20.5 mm. Position of stigma an average of 1.3 mm below anthers. Surface — pubescent. Color varies from 10Y 7/8 to 7.5Y 7/10.

*Fragrance*.—Wanting.

*Color*.—Varies from 2.5RP 9/2 to 5RP 8/4.

*Pedicel*.—Average length 7.6 mm. Average width 1.6 mm. Surface — glabrous. Color varies from 5GY 6/8 to 10R 3/8.

*Number flowers per flower bud*.—Normally one.

Fruit:

*Maturity when described*.—Firm ripe and ready for consumption.

*Date of first picking*.—Apr. 25, 2017.

*Date of last picking*.—May 5, 2017, varies slightly with climatic conditions.

*Size*.—Large. Average diameter axially 66.6 mm. Average transversely in suture plane 68.3 mm. Average weight 178.9 grams, varies slightly with fertility of the soil, amount of thinning and climatic conditions.

*Form*.—Globose.

*Suture*.—Nearly smooth, some fruit with slight suture.

*Ventral surface*.—Nearly smooth.

*Apex*.—Slightly retuse, some fruit with slight tips.

*Base*.—Retuse.

*Stem cavity*.—Rounded to slightly elongated in suture plane. Average depth 6.3 mm. Average diameter 7.1 mm.

Stem:

*Size*.—Medium. Average length 10.7 mm. Average diameter 3.3 mm.

*Color*.—Varies from 2.5GY 5/8 to 5GY 5/8.

Flesh:

*Ripens*.—Fairly even, some fruit slightly earlier at apex.

*Texture*.—Firm, meaty, crisp.

*Fibers*.—Few, small, tender.

*Firmness*.—Good, comparable to other commercial peach varieties.

*Aroma*.—Moderate.

*Amydgalin*.—Undetected.

*Eating quality*.—Good.

*Flavor*.—Good.

*Juice*.—Moderate amount, enhances flavor.

*Acidity*.—Not available.

*Brix*.—Average Brix 9.5°, varies slightly with amount of fruit per tree and climatic conditions.

*Color*.—Varies from 5Y 8.5/10 to 7.5Y 8/10.

*Pit cavity*.—Average length 36.0 mm. Average width 30.0 mm. Average depth 13.0 mm. Color varies from 7.5Y 8/8 to 10Y 8.5/6.

Skin:

*Thickness*.—Medium.

*Surface*.—Smooth.

*Pubescence*.—Moderate amount, short in length.

*Tendency to crack*.—None.

*Color*.—Ground color varies from 7.5Y 8/8 to 10Y 8.5/6. Overspread with 7.5R 3/8 to 10R 2/6.

*Tenacity*.—Tenacious to flesh.

*Astringency*.—None.

Stone:

*Type*.—Clingstone, strong adherence to flesh.

*Size*.—Large. Average length 35.0 mm. Average width 29.0 mm. Average thickness 25.1 mm.

*Form*.—Ovoid.

*Base*.—Flat.

*Apex*.—Rounded.

*Surface*.—Pitted throughout, pits vary from round to elongated.

*Sides*.—Unequal, one side extending further from suture plane.

*Ridges*.—Small, narrow ridges extending from base toward apex.

*Tendency to split*.—Slight.

*Color*.—Varies from 7.5YR 7/6 to 7.5YR 6/6.

Kernel:

*Size*.—Medium. Average length 19.2 mm. Average width 11.1 mm. Average depth 6.6 mm.

*Form*.—Ovoid.

*Viability*.—Partially viable, incomplete embryo development.

*Skin color*.—Varies from 7.5Y 9/2 to 7.5Y 9/4 when dry.

Use:

*Dessert*.—Market — local and long distance.

Keeping quality: Good, held firm in cold storage 2 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

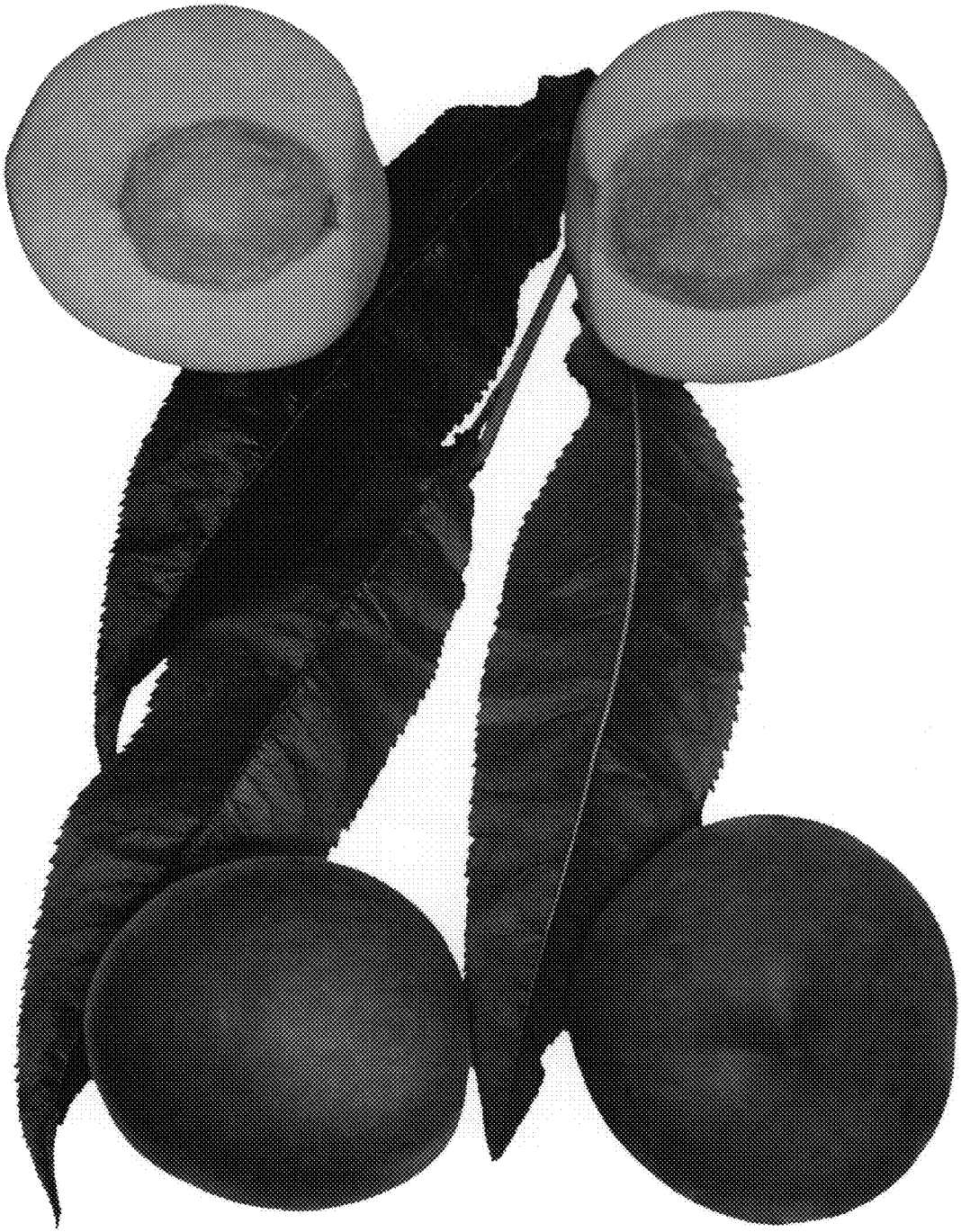

* * * * *